United States Patent [19]

Williams et al.

[11] Patent Number: 4,622,403

[45] Date of Patent: Nov. 11, 1986

[54] 6-H DIBENZ[B,F]THIEPIN COMPOUNDS

[75] Inventors: Haydn Williams, Dollard des Ormeaux; Joshua Rokach, Laval, both of Canada

[73] Assignee: Merck Frosst Canada, Inc., Province of Quebec, Canada

[21] Appl. No.: 540,480

[22] Filed: Oct. 11, 1983

[51] Int. Cl.⁴ .......................................... C07D 409/02
[52] U.S. Cl. .................................... 548/252; 548/135; 548/418; 549/12
[58] Field of Search .................. 549/12; 548/250, 252, 548/127, 135, 253, 418

[56] References Cited

U.S. PATENT DOCUMENTS 4,237,160 12/1980 Hamel .................................. 424/275
4,386,098 5/1983 Woltersdorf, Jr. ................. 424/270
4,386,103 5/1983 Pogany .............................. 424/313
4,394,515 7/1983 Rokach .................................. 549/12

FOREIGN PATENT DOCUMENTS 11067 5/1980 European Pat. Off. .
29587 6/1981 European Pat. Off. .

OTHER PUBLICATIONS

Progress in Drug Research, vol. 5, 1963, p. 371, L. H. Sarett et al.

Primary Examiner—Christopher Henderson
Attorney, Agent, or Firm—C. M. Caruso; G. J. Lopez; H. J. Pfeiffer

[57] ABSTRACT

Novel dibenz[b,f]thiepin derivatives are employed in the treatment and control of allergic conditions such as allergic asthma.

29 Claims, No Drawings

6-H DIBENZ[B,F]THIEPIN COMPOUNDS

BACKGROUND OF THE INVENTION

This invention relates to new and useful compositions of matter classifiable in the field of organic chemistry as derivatives of dibenzthiepins. More particularly, the instant invention relates to a novel group of dibenz[b,f]-thiepins having a fourth ring of five or six carbon atoms, fused to the main ring system e.g., benz[b]indeno[f]thiepins; to methods of preparing such compounds; and to the method of employing them in the treatment and control of allergic conditions such as asthma.

SUMMARY OF THE INVENTION

In its composition aspect, therefore, the instant invention may be described as residing in the concept of dibenz[b,f]thiepins characterized by having the following structural formulae:

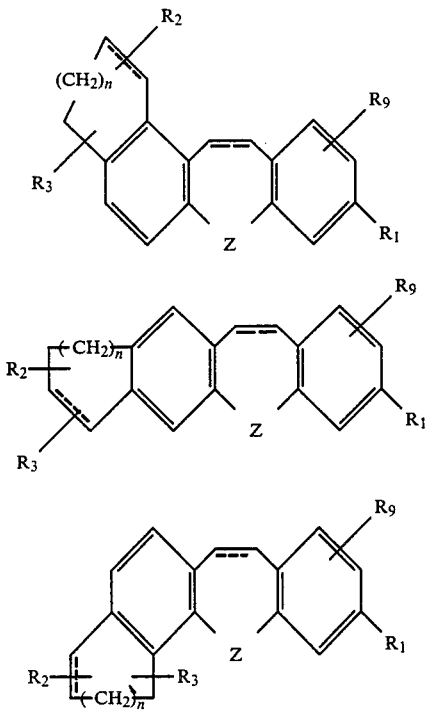

wherein n is 1 or 2, the broken lines represents optional double bonds and Z is a member selected from the group consisting of thio, sulfinyl or sulfony; $R_2$, $R_3$ and $R_9$ are each independently selected from the group consisting of hydrogen, halogen, nitro, loweralkyl, amino, N-loweralkylamino, N,N-diloweralkylamino, loweralkanoyl, hydroxy, loweralkoxy, loweracyloxy, loweralkylthio, trifluoromethylthio, loweralkylsulfinyl, loweralkylsulfonyl, trifluoromethyl or together $R_2$ and $R_3$ can be a doubly bonded oxygen; and $R_1$ is a member selected from the groups consisting of:

(a) 5-tetrazolyl, 5-tetrazolylmethyl, 3-hydroxy-1,2,5-thiadiazol-4-yl, 4-hydroxy-$\Delta^3$-pyrroline-3-yl-2,5-dione or

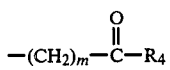

wherein m is an integer from 0–4 and $R_4$ is a member selected from the group consisting of hydroxy, loweralkoxy, N,N-diloweralkylaminoloweralkoxy, hydroxyloweralkoxy, carboxyloweralkoxy, amino, N-loweralkylamino, N,N-diloweralkylamino, loweralkylsulfonylamino, carboxyloweralkylamino, carboxamidoloweralkylamino, 2-imino-3-methylthiazolidine, loweracyloxyloweralkoxy or (5-methyl-2-oxo-1,3-dioxolen-4-yl)methoxy;

(b) —CHO or a prodrug derivative of an aldehyde having the formulae:

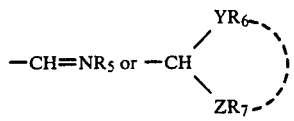

wherein $R_5$ is a member selected from the group consisting of hydrogen, loweralkyl, aryl, hydroxy, loweralkoxy, loweracyloxy, amino or loweralkylamino; Y and Z are each independently oxygen, sulfur or $NR_6$ and $R_6$ and $R_7$ are each independently hydrogen or loweralkyl; R6 and R7 may optionally be joined to form a ring of 5–8 members.

(c) —(CH2)n-OR8 wherein n is 0–4 and $R_8$ is a member selected from hydrogen loweracyl, loweralkylaminolacyl, loweralkylcarboxy, loweralkylcarboxamido, loweralkylcarboxamidoacyl or loweracyloxyloweralkyl; and the pharmaceutically acceptable salts thereof.

DETAILED DESCRIPTION

As used herein, the term, halogen, includes chlorine, bromine, iodine and fluorine. The terms, loweralkyl, loweracyl and loweralkoxy, wherever employed, include straight and branched chain alkyl, loweracyl and alkoxy groups having 1 to 5 carbon atoms in the alkyl, acyl or alkoxy moiety such as, for example, methyl, ethyl, isopropyl, butyl 2,2-dimethypropyl, ethoxy, propoxy and isobutoxy. The term, loweralkanoyl, includes straight and branched chain alkanoyl groups of 1 to 5 carbon atoms including, for example, formyl, acetyl, propanoyl, butyryl and 2,2-dimethylpropanoyl.

The instant invention is based upon applicants' discovery that the dibenz[b,f]thiepins of Formulae Ia, Ib and Ic markedly antagonize the actions of contractile prostaglandins such as $PGF_{2\alpha}$, $PGG_2$, $PGH_2$ and $TXA_2$. The use of the dibenz[b,f]thiepins of this invention, which act as prostaglandin antagonists and biosynthesis inhibitors, offers a new approach to therapy in a variety of allergic conditions such as allergic asthma where excessive contractile activity of prostaglandins and prostaglandin biosynthetic intermediates occur. It is well known, for example, that prostaglandins such as $PGF_{2\alpha}$, $PGG_2$, $TXA_2$ and $PGH_2$ are potent contractants of bronchial muscle and that human asthmatics are especially sensitive to the bronchial constricting action of $PGF_{2\alpha}$. The antagonizing action of the dibenz[b,f]-thiepins of this invention against the constricting actions of contractile prostaglandins has been confirmed in vitro and in vivo using standard pharmacological techniques. It is contemplated, therefore, that the dibenz[b,f]thiepins of this invention will be employed in dosage unit form as the essential active ingredient in pharmaceutical formulations intended for the treatment and control of allergic conditions such as asthma in humans and warm blooded animals.

The dibenz[b,f]thiepin derivatives of this invention may be prepared in any manner available to the skilled artisan. One such method is presented in Scheme I.

f]thiepin-7-carboxylic acid by treatment with potassium hydroxide and hydrazine hydrate.

Dehydration of the 11-hydroxy compound may be

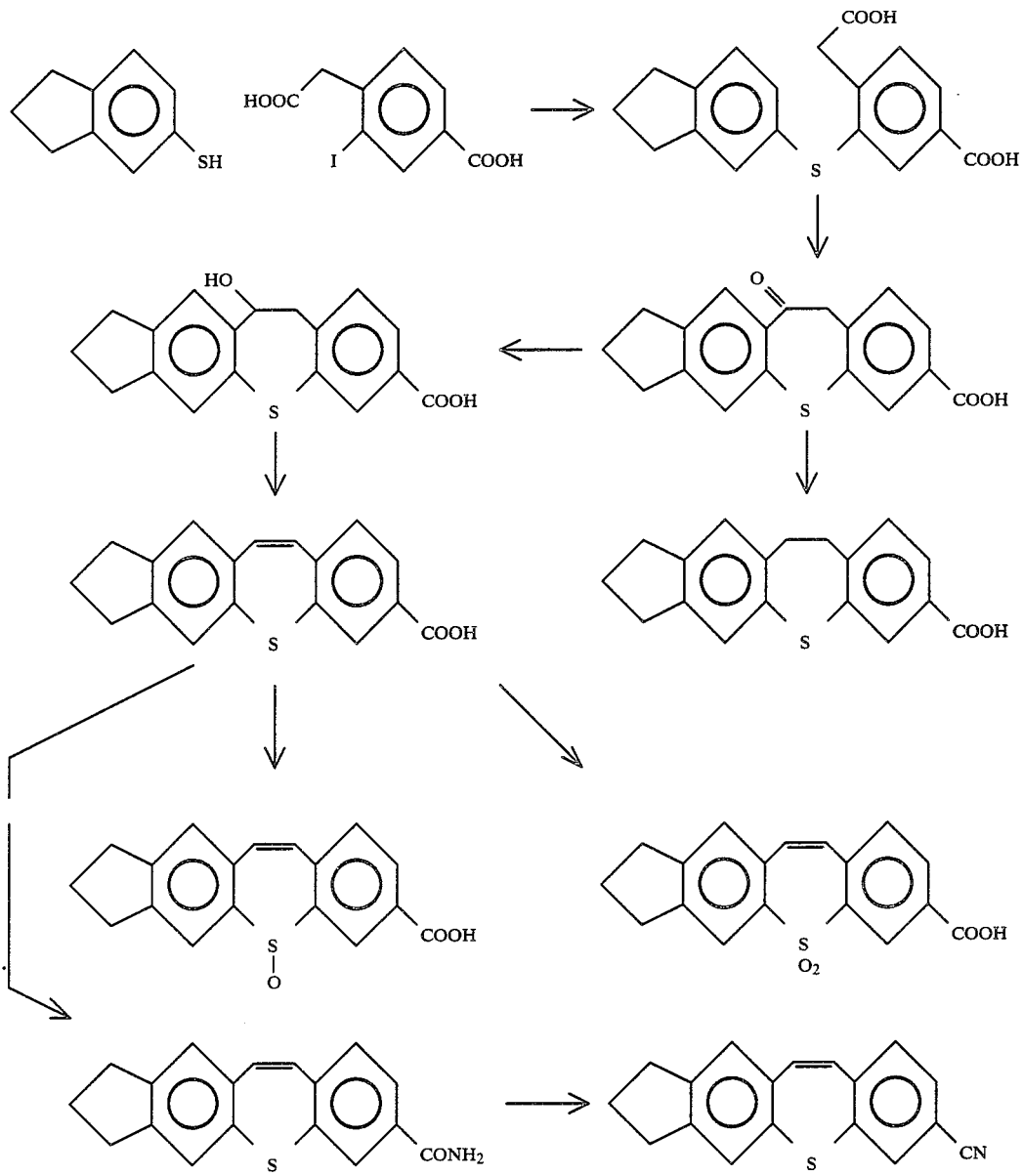

Scheme I

5-Mercaptoindan is reacted with 4-carboxy-2-iodophenylacetic acid in the presence of a strong base such as potassium hydroxide affording an indanylthiophenylacetic acid compound.

The indanylthiophenylacetic acid compound may be cyclized by treatment with (1) trifluoroacetic acid and (2) trifluoroacetic anhydride. Reduction of the 11-oxo compound to the 11-hydroxy compound is accomplished by conventional reducing agents, such as sodium borohydride.

The 11-oxo compound may be converted to the compound 2,3,10,11-tetrahydro-1H-benzo[b]indeno [5,6,- accomplished by treatment with a strong acid such as sulfuric acid, affording the compound 2,3-dihydro-1H-benzo[b]indeno[5,6-f]thiepin-7-carboxylic acid.

Oxidation of the carboxylic acids using mild oxidation conditions affords the 5-oxide compound, while more vigorous conditions yield the 5,5-dioxide species.

The carboxylic acids may be converted to a number of derivatives as discussed in greater detail below.

In addition to the reactions outlined in Scheme I, the compounds of the present invention may be prepared as outlined in Scheme II.

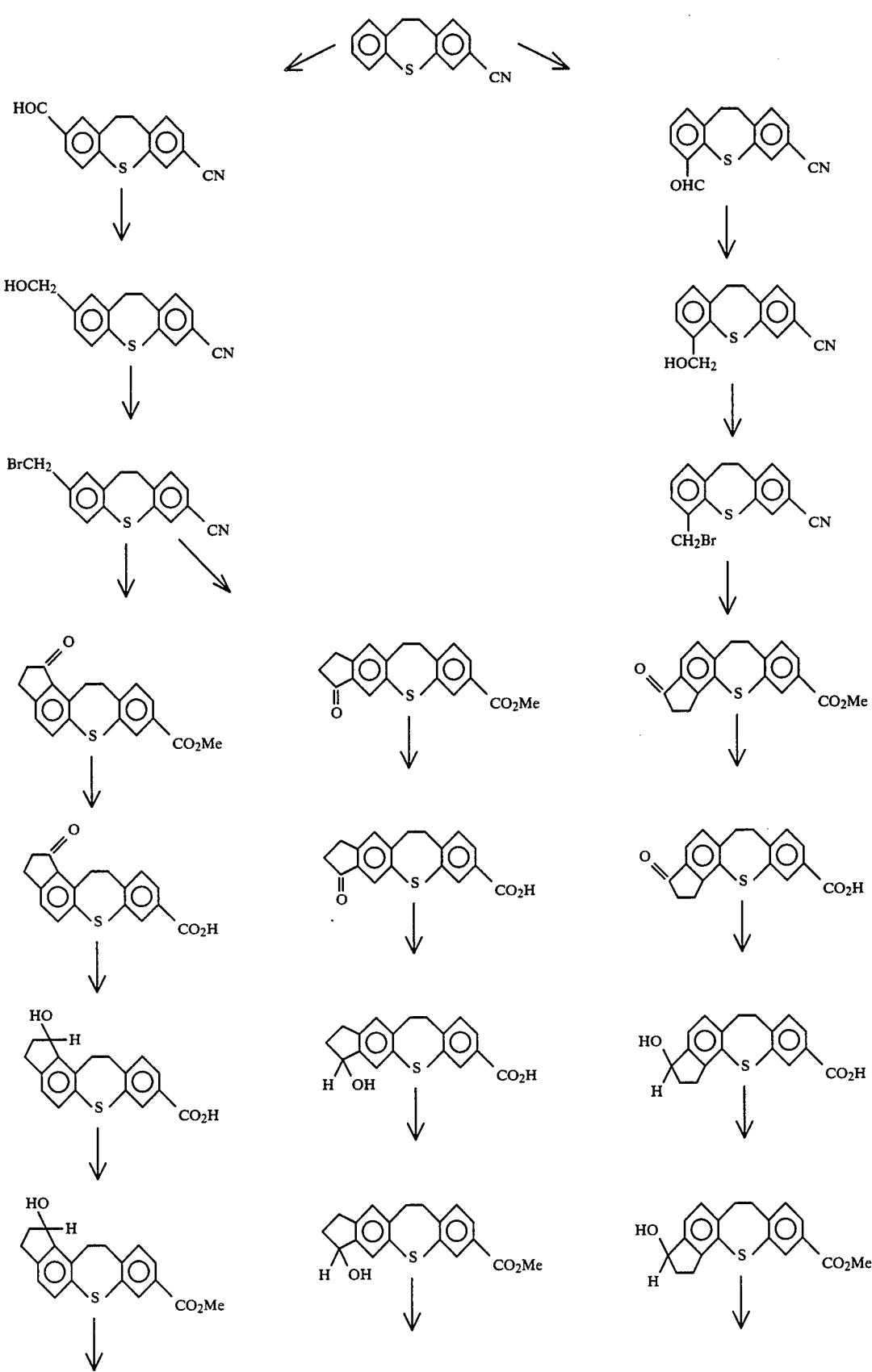
Scheme II

-continued
Scheme II

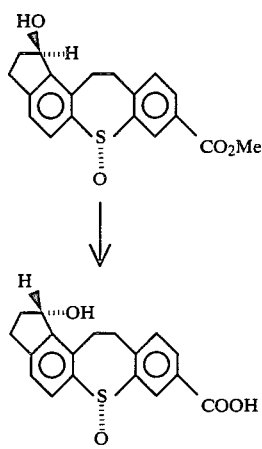

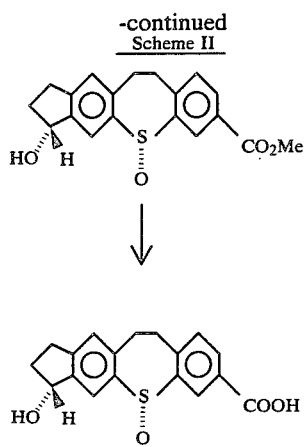

3-Cyano-10,11-dihydrodibenz[b, f]thiepin (see compound XXVII, European Patent Appln. No. 11,067) may be reacted with dichloromethyl methylether to yield the 6-formyl- and 8-formyl-3-cyano compounds The formyl compounds may be reduced with sodium borohydride to produce the 6-hydroxymethyl and 8-hydroxymethyl compounds.

Bromination of the 6- or 8-hydroxymethyl compounds may be accomplished by treatment with phosphorus tribromide Reaction of the 6- or 8-bromo methyl compounds with diethyl malonate and sodium hydride, followed by (1) heating; (2) hydrolysis; and (3) cyclization, afforded the oxo-tetrahydro-1H-benz[b]indenothiepin compounds shown.

Reduction of the 1-oxo group may be accomplished using a reducing agent such as sodium borohydride, affording the (±) hydroxy derivatives. These compounds may then further be derivatized and/or resolved into the separate enantiomorphs.

In addition to their therapeutic properties as noted above, the carboxylic acid derivatives of this invention serve as valuable intermediates in the preparation of other variously substituted and therapeutically useful dibenz[b,f]thiepins of formula Ia, Ib or Ic. Thus, the carboxylic acid of formula Ia, Ib or Ic may be converted readily into the corresponding acid halide, preferably the acid chloride, by treating the carboxylic acid with a thionyl halide, preferably thionyl chloride. The resulting halocarbonyldibenz[b,f]thiepin (i.e., the chlorocarbonylcompounds of formula Ia, Ib or Ic) then may be treated with various well-known reagents to form desired ester and amide derivatives Thus, for example, the chlorocarbonyl compounds of formula Ia, Ib or Ic may be treated:

(a) with a loweralkanol such as, for example, methanol, ethanol, 2-propanol, butanol and 2-butanol, to form the corresponding loweralkyl esters;

(b) with ammonia to form the carboxamides;

(c) with an N-loweralkylamine such as, for example, methylamine, ethylamine, propylamine, isopropylamine and butylamine, or an N,N-diloweralkylamine such as, for example, dimethylamine, diethylamine, dipropylamine and dibutylamine, to form the corresponding N-loweralkylcarboxamide or N,N-diloweralkylcarboxamide;

(d) with a loweralkylsulphonamide such as for example, methanesulphonamide, ethanesulphonamide, propanesulphonamide and butanesulphonamide, to form the corresponding N-loweralkylsulfonylcarboxamide;

(e) with 2-imino-3-methylthiazolidine to form the corresponding (3-methyl-2-thiazolidinylidene) carboxamide;

(f) with a loweralkyldiol such as, for example ethylene glycol, trimethylene glycol and 1,4-butanediol, to form the corresponding hydroxyloweralkylester;

(g) with an N,N-diloweralkylaminoloweralkanol such as, for example, N,N-dimethylethanolamine, N,N-diethylethanolamine, 3-N,N-dimethylaminopropan-1-ol and 4-N,N-diethylaminobutan-1-ol, to form the corresponding N,N-diloweralkylaminolower-alkyl ester;

(h) with an amino acid such as, for example, glycine, alanine and valine, to form the corresponding N-carboxyloweralkylcarboxamide;

(i) with an alkali metal salt of a hydroxyloweralkanoic acid such as, for example, hydroxyacetic acid, 3-hydroxybutyric acid and β-hydroxypropionic acid, to form the corresponding carboxyloweralkyl ester.

Formation of the 5-oxide or the 5, 5-dioxide groups (e.g., preparation of the sulfinyl or sulfonyl compounds of the instant invention) conveniently is achieved by controlled oxidation techniques. Thus, for example, the carboxylic acid derivatives of formulae Ia, Ib or Ic may be oxidized with hydrogen peroxide in the presence of an acidic solvent such as acetic acid or with organic peroxides such as peroxy acids, for example, m-chloroperbenzoic acid and the like, in a stepwise fashion to form the corresponding sulfinyl derivative, formula Ia, Ib or Ic, and sulfonyl derivative, formulae Ia, Ib or Ic. The molar ratio of oxidant to reductant determines the oxidation level of the sulfur in the product. A 1:1 molar ratio, for example, results largely in the production of the sulfinyl derivative whereas a 2 to 3 molar excess of oxidant results in a yield predominantly comprising the sulfonyl derivative.

As noted above, pharmaceutically acceptable salts of the novel dibenz[b,f]thiepins also are included within the scope of this invention. The term, pharmaceutically acceptable salts, is intended to include salts derived from pharmaceutically acceptable non-toxic acids and bases such as, for example, ammonium salts, alkali metal salts such as sodium and potassium salts, alkaline earth metal salts such as magnesium and calcium salts, salts of organic bases such as amine salts derived from mono-, di and triloweralkyl or loweralkanoyl amines such as trimethylamine, dimethylamine and triethanolamine, salts derived from heterocyclic amines such as piperidine, 1-methylpiperazine, piperazine and morpholine, and salts derived from pharmaceutically acceptable acids such as hydrochloric acid, sulfuric acid, tartaric acid and propionic acid.

The dibenz[b,f]thiepins of formulae Ia, Ib and Ic are useful in the treatment and prophylaxis of human or warm-blooded animal disease conditions where excessive undesirable contractile activity of prostaglandins, such as $PGF_{2\alpha}$, or prostaglandin biosynthetic intermediates contribute. In particular, they are of value in the treatment and control of allergic conditions such as asthma.

The magnitude of a prophylactic or therapeutic dose of compound of formulae Ia, Ib and/or Ic will, of course, vary with the nature and the severity of the condition to be treated and with the particular compound of formulae Ia, Ib and Ic and its route of administration. In general, the dose range lies within the range of 0.2 mg to 100 mg per kg body weight per day.

The pharmaceutical compositions of the present invention comprise a compound of formula Ia, Ib and/or Ic as an active ingredient, and may also contain pharmaceutically acceptable carrier and optionally other therapeutic ingredients. The compositions include compositions suitable for oral, rectal, opthalmic, pulmonary, nasal, dermal, topical or parenteral (including subcutaneous, intramuscular and intravenous) administration, although the most suitable route in any given case will depend on the nature and severity of the condition being treated and on the nature of the active ingredient. They may be conveniently presented in unit dosage form and prepared by any of the methods well known in the art of pharmacy.

For use where a composition for intravenous administration is employed, a suitable dosage range is from 0.2 to 10 mg (preferably 1 to 8 mg) of a compound of formula Ia, Ib or Ic per kg of body weight per day. In the case where an oral composition is employed a suitable dosage range is about, e.g., 1 to 50 mg of a compound of formula Ia, Ib or Ic per kg of body weight per day, preferably from 10 to 40 mg/kg.

Pharmaceutical compositions of the present invention suitable for oral administration and by inhalation in the case of asthma therapy may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of tne methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of powdered compound moistened with an inert liquid diluent. Desirably, each tablet contains from 50 mg to 500 mg of the active ingredient and each cachet or capsule contains from 50 mg to 500 mg of the active ingredient The best mode contemplated by applicants for carrying out their invention is illustrated in the following working examples. No limitation, however, is intended except as set forth in the appended claims.

EXAMPLE 1

4-Carboxy-2-(5-indanylthio)-phenylacetic acid

To 50% aqueous potassium hydroxide solution (500 g) under argon was added 5-mercaptoindan (30.0 g, 0.2 mole) and copper powder (16.3 g). Then 4-carboxy-2-iodophenylacetic acid (38.25 g, 0.125 mole) was added with mechanical stirring and the reaction mixture was stirred under reflux (oil-bath 140°–145° C.) for 3 hours. The mixture was diluted with ice-water (800 ml), filtered, and the filtrate was treated with charcoal and refiltered. Acidification of the alkaline solution precipitated a solid which was collected, washed well with water and drained thoroughly on the filter. The solid was stirred with hexane (200 ml) to remove mercaptoindane and was refiltered to yield 33.55 g.

The product was recrystallized from acetic acid and then had a melting point of 225°–228° C.

Analysis for $C_{18}H_{16}O_4S$:

Requires: C 65.84, H 4.91, S 9.76; Found: C 65.64, H 4.97, S 9.70.

EXAMPLE 2

11-Oxo-2,3,10,11-tetrahydro-1H-benzo[b]indeno[5,6-f]thiepin-7-carboxylic acid

4-Carboxy-2-(5-indanylthio)phenylacetic acid (33.55 g, 0.102 mole) was added to trifluoroacetic acid (200 ml) and to the stirred suspension was added, slowly with stirring, trifluoroacetic anhydride (200 ml). After stirring the mixture for 48 hours at room temperature, the mixture was poured slowly onto ice (200 g), and the slurry was diluted to about 1 liter before collecting the crude product. The dried solid was stirred in suspension in acetonitrile for 45 minutes, refiltered and dried to yield 24.95 g.

The compound was recrystallized from dimethylformamide/acetonitrile and then had a melting point of 275°–277° C. dec.

Analysis for $C_{18}H_{14}O_3S$: Requires: C 69.68, H 4.55, S 10.32; Found: C 69.40, H 4.62, S 10.52.

EXAMPLE 3

11-Hydroxy-2,3,10,11-tetrahydro-1H-benzo[b]indeno[5,6-f]thiepin-7-carboxylic acid 11-Oxo-2,3,10-11-tetrahydro-1H-benzo[b]indeno [5,6-f]thiepin-7-carboxylic acid (24.75 g, 0.0798 mole) was suspended in water (495 ml) and 5N sodium hydroxide (17.6 ml) was added with stirring. The resulting suspension of sodium salt was treated with sodium borohydride (9.10 g, 0.24 mole) in 1 g portions and the mixture was stirred at room temperature overnight. Then the mixture was acidified carefully (frothing) with 6N hydrochloric acid. The suspension was stirred for 20 minutes after completion of the acidification and the solid as collected, washed well with water, and dried to yield 24.44 g.

The ammonium salt of the acid was crystallized from hot water and the title compound obtained by acidification of the salt had a melting point of 202°–203° C. dec.

Analysis for $C_{18}H_{16}O_3S$: Requires: C 69.21, H 5.16, S 10.26; Found: C 69.52, H 5.33, S 10.14.

EXAMPLE 4

2,3-Dihydro-1H-benzo[b]indeno[5,6-f]thiepin-7-carboxylic acid

11-Hydroxy-2,3,10,11-tetrahydro-1H-benzo[b]indeno[5,6-f]thiepin-7-carboxylic acid (11.3 g, 36.2 mmole) was suspended in acetic acid (225 ml) heated in an oil-bath at 115° C. Concentrated sulfuric acid (22.5 ml) was added in a thin stream. The suspension was heated in the oil-bath for 1 hour and allowed to cool. The crude product was filtered off and washed with methanol to yield 10.14 g.

The title compound was purified by filtering a solution of the solid in a large volume of boiling acetic acid and evaporating the filtrate to a smaller volume, and the title compound had a melting point of 268°–271° C. dec.

Analysis for $C_{18}H_{14}O_2S$: Requires: C 73.44, H 4.79, S 10.89; Found: C 73.23, H 5.01, S 10.78.

The ethyl ester of the title compound had a melting point of 103°–104° C.

EXAMPLE 5

2,3-Dihydro-1H-benzo[b]indeno[5,6-f]thiepin-7-carboxylic acid 5,5-dioxide 2,3-Dihydro-1H-benzo[b]indeno[5,6-f]thiepin-7-carboxylic acid (2.97 g, 10.1 mmole) was suspended in trifluoroacetic acid (60 ml) and the stirred suspension was treated at 0°–5° C. with 50% hydrogen peroxide in small increments. The formation of the 5-oxide and then of the 5,5-oxide can be followed by thin layer chromatography.

NOTE: Sulfone can be distinguished from sulfoxide and starting material on Quantum silica gel plates developed with 100:10:1 toluene/dioxane/acetic acid. Starting material was distinguished from sulfoxide and sulfone on Eastman silica gel sheet developed with the same solvent mixture. Sulfoxide and sulfone fluoresced differently.

Conversion to the title compound requires about 1.8 ml of 50% hydrogen peroxide. The solution was evaporated to about 25 ml and poured into water (100 ml). The aqueous layer was decanted from the sticky precipitate which crystallized on stirring with hot acetic acid (10 ml) to afford 1.618 g of crude product. This was recrystallized from hot acetic acid to give the title compound 1.23 g with a melting point of 298°–301° C. dec.

Analysis for $C_{18}H_{14}O_4S$: Requires: C 66.24, H 4.32, S 9.82; Found: C 66.21, H 4.49, S 9.77.

EXAMPLE 6

2,3-Dihydro-1H-benzo[b]indeno[5,6-f]thiepin-7-carboxylic acid 5-oxide

Repeating the procedure of Example 5 but using a little less than half of the equivalent amount of 50% hydrogen peroxide provides the title compound.

EXAMPLE 7

5-(2,3-Dihydro-1H-benzo[b]indeno[5,6-f]thiepin-7-yl)tetrazole

STEP A Preparation of 2,3-dihydro-1H-benzo[b]indeno[5,6-f]thiepin-7-carboxamide

A mixture of 2,3-dihydro-1H-benzo[b]indeno[5,6-f]thiepin-7-carboxylic acid (6.00 g, 20.4 mmole) and thionyl chloride (24 ml) was heated slowly to reflux during 30 minutes and maintained at reflux for another 30 minutes. Excess thionyl chloride was distilled off and the residue was evaporated twice with benzene. The crude acid chloride was suspended in dry ether (150 ml) and a concentrated solution of ammonia in dry ether was added slowly with stirring. Ammonia was passed through the mixture for one hour and the solid was collected. The solid was stirred in suspension in a solution of ammonia in methanol (30 ml) and refiltered to afford 4.66 g (78%) of the title compound as an extremely insoluble solid.

STEP B Preparation of 2,3-dihydro-1H-benzo[b]indeno[5,6-f]thiepin-7-carbonitrile The crude amide from Step A (4.34 g, 14.8 mmole) in pyridine (43.5 ml) was treated slowly under cooling (ice-bath) with trifluoroacetic anhydride (8.7 ml). The mixture was stirred for 1 hour at ambient temperature and then poured into a mixture of ice (400 g) and concentrated hydrochloric acid (50 ml). The product was extracted into ether and the ethereal extract was washed with water, then with 10% sodium carbonate solution and finally with saturated sodium chloride solution. After drying ($MgSO_4$) the solution was evaporated to a tan colored solid (3.22 g). The product was purified by chromatography on Merck silica gel using toluene as solvent to give 2.45 g of the title compound. Melting point 142°–143° C. (from acetonitrile).

Analysis for $C_{18}H_{13}NS$: Requires: C 78.51, H 4.76, N 5.09, S 11.64; Found: C 78.36, H 4.71, N 5.30, S 11.27.

STEP C Preparation of 5-(2,3-dihydro-1H-benzo[b]indeno[5,6-f]thiepin-7-yl)tetrazole A solution of 2,3-dihydro-1H-benzo[b]indeno[5,6-f]thiepin-7-carbonitrile (2.10 g, 7.625 mmole) in dimethylformamide (31.5 ml) stirred under reflux (oil-bath at 170°–180° C.) in an atmosphere of argon was treated with a mixture of sodium azide (743 mg, 11.44 mmole) and ammonium chloride (612 mg, 11.44 mmole). An equal portion of sodium azide and ammonium chloride was added after 1 hour and then at 30 minute intervals seven portions of a mixture of sodium azide (247 mg, 3.81 mmole) and ammonium chloride (204 mg, 391 mmole) were added. After heating for a further 1 hour the reaction mixture was allowed to cool, then it was diluted with water (150 ml) and acidified. An extraction with methylene chloride (250 ml) was performed. The methylene chloride solution was extracted with a mixture of water (100 ml) and 5N sodium hydroxide (10 ml) and after a further wash with water the combined aqueous extract on acidification yields 1.555 g of title compound.

Work up of the methylene chloride solution gave 832 mg of unreacted nitrile which on recycling through the reaction affords another 426 mg of product.

Thus the combined yield of 5-(2,3-dihydro1H-benzo[b]indeno[5,6-f]thiepin-2-yl)tetrazole was 1.98 g (81%). The tetrazole was purified by suspending the solid in hot 50% aqueous methanol, adding sufficient ammonium hydroxide to dissolve the solid, treating the solution with charcoal and filtering and then acidifying the filtrate with acetic acid. The compound thus purified had a melting point of 238°–240° C. dec.

Analysis for $C_{18}H_{14}N_4S$: Requires: C 67.90, H 4.43, N 17.60, S 10.09; Found: C 67.75, H 4.76, N 17.48, S 10.14.

EXAMPLE 8

5-(2,3-Dihydro-5-oxido-1H-benzo[b]indeno[5,6-f]thiepin-7-yl)-tetrazole

A suspension of 5-(2,3-dihydro-1H-benzo[b]indeno[5,6-f]thiepin-7-yl)tertrazole (1.039 g, 3.27 mmole) in acetic acid (40 ml) at 70° C. was treated slowly with stirring with a solution of 50% hydrogen peroxide in acetic acid (68 mg per ml). After the addition of 7.2 ml of oxidizing agent a barely detectable (by tlc) amount of starting material remained. The mixture was cooled and the solid was collected. It was purified by stirring in suspension in hot methanol (22 ml) and filtering hot to obtain the title compound, 781 mg (71%), m.p. 273° dec.

Analysis for $C_{18}H_{14}N_4OS$ Required: C 64.65, H 4.22, N 16.75, S 9.59; Found: C 64.81, H 4.26, N 16.66, S 9.55.

EXAMPLE 9

5-(2,3-Dihydro-5,5-dioxido-1H-benzo[b,f]thiepin-7-yl)-tetrazole

Repeating the procedure of Example 8 but using a little more than twice the equivalent quantity of 50% hydrogen peroxide provides the title compound).

EXAMPLE 10

2,3,10,11-Tetrahydro-1H-benzo[b]indeno[5,6-f]thiepin-7-carboxylic acid

A mixture of 11-oxo-2,3,10,11-tetrahydro-1H-benzo[b]indeno[5,6-f]thiepin-7-carboxylic acid (10.0 g 34 mmole), 85% potassium hydroxide (7.5 g), 100% hydrazine hydrate (5 ml) and diethylene glycol (200 ml) was heated under nitrogen, in an oil-bath at 225° C. for 4 hours. The cool reaction mixture was diluted with water and acidified with 6N hydrochloric acid. The solid was collected by filtration, and after drying on the filter it was stirred in suspension in a mixture of ethyl acetate (50 ml) and methanol (10 ml). The crude product was collected and dried. 9.47 g.

Analytically pure title compound was obtained in about 70% yield by recrystallization of the crude product from a mixture of dimethylformamide and acetonitrile, and then had a m.p. of 264° dec.

Analysis for $C_{18}H_{16}O_2S$ Require: C 72.94, H 5.44, S 10.82; Found: C 72.82, H 5.50, S 10.88.

EXAMPLE 11

2,3,10,11-Tetrahydro-1H-benzo[b]indeno[5,6-f]-thiepin-7-carboxylic acid 5-oxide

STEP A: Preparation of methyl 2,3,10,11-tetrahydro-1H-benzo[b]indeno[5,6-f]-thiepin-7-carboxylate A suspension of crude 2,3,10,11-tetrahydro-1H-benzo[b]indeno[5,6-f]thiepin-7-carboxylic acid (8.276 g, 28 mmole) in methanol (200 ml) containing concentrated sulfuric acid was stirred under reflux for 20 hours. The suspension was evaporated, water was added and the product was extracted with chloroform. The crude ester was purified by chromatography (250 g Merck silica gel eluted with 1:1 hexane/methylene chloride) The title compound had m.p. 110°–111° C. (from acetonitrile).

Analysis for $C_{19}H_{18}O_2S$ Requires: C 73.52, H 5.84, S 10.33; Found: C 73.79, H 6.17, S 9.99.

STEP B: Preparation of methyl 2,3,10,11-tetrahydro-1H-benzo[b]indeno[5,6-f]-thiepin-7-carboxylate 5-oxide To a solution of methyl 2,3,10,11-tetrahydro1H-benzo[b]indeno[5,6-f]thiepin-7-carboxylate (3.05 g; 9.84 mmole) in methylene chloride (200 ml) stirred in a cooling bath at 0°–5° C. was added 85% m-chloroperbenzoic acid (2.00 g; 9.85 mmole) in small portions during 1 hour. After stirring the reaction mixture for 30 minutes at room temperature, more methylene chloride was added to get a clear solution and then calcium hydroxide (4 g) was added. The suspension was stirred for 25 minutes, filtered and evaporated. The crude product was purified by column chromatography (Merck silica gel eluted with 1:4 ethyl acetate/toluene) to yield 2.121 g (66%) of the title compound, m.p. 150°–154° C. (from MeCN).

Analysis for $C_{19}H_{18}O_3S$ Requires: C 69.91, H 5.56, S 9.82; Found: C 69.96, H 5.70, S 10.13.

STEP C: Preparation of 2,3,10,11-tetrahydro-1H-benzo[b]indeno[5,6-f]-thiepin-7-carboxylic acid 5-oxide Methyl 2,3,10,11-tetrahydro-1H-benzo[b]indeno[5,6-f]thiepin-7-carboxylate 5-oxide (2.00 g; 6.13 mmole) was added to a solution of 85% potassium hydroxide (808 mg; 12.26 mmole) in a mixture of water (8 ml) and ethanol (40 ml) at room temperature. After 1 hour, the solution was filtered, evaporated to 15 ml and acidified to pH 2 with hydrochloric acid. The product was collected, washed with water and dried (finally at 105° C./0.005 Torr) to yield 1.55 g (81%) with a m.p. 290°–294° dec.

Analysis for $C_{18}H_{16}O_3S$ Requires: C 69.21, H 5.16, S 10.26; Found: C 69.13, H 5.17, S 10.31.

EXAMPLE 12

2,3,10,11-Tetrahydro-1H-benzo[b]indeno[5,6-f]thiepin-7-carboxylic acid 5,5-dioxide

STEP A: Preparation of methyl 2,3,10,11-tetrahydro-1H-benzo[b]indeno[5,6-f]thiepin-7-carboxylate 5,5-dioxide Repeating the procedure of Example 11, Step B, but using slightly more than the two equivalents of m-chloroperbenzoic acid and a correspondingly greater amount of calcium hydroxide, provides the title compound.

STEP B: Preparation of 2,3,10,11-tetrahydro-1H-benzo[b]indeno[5,6-f]-thiepin-7-carboxylic acid 5,5-dioxide Repeating the procedure of Example 11, Step C, but using methyl 2,3,10-11-tetrahydro-1H-benzo[b]indeno[5,6-f]thiepin-7-carboxylate 5,5-dioxide in place of methyl 2,3,10,11-tetrahydro-1H-benzo[b]indeno[5,6-f]thiepin-7-carboxylate 5-dioxide provides the title compound.

EXAMPLE 13

3-Cyano-6-formyl-10,11-dihydrodibenzo[b,f]thiepin
and
3-Cyano-8-formyl-10,11-dihydrodibenzo[b,f]thiepin Anhydrous aluminium chloride (37.8 g; 0.283 mole was added to a stirred solution of 3-cyano-10,11-dihydrodibenzo[b,f]thiepin (32.0 g; 0.135 mole) in dry 1,2-dichloroethane (325 ml) with cooling (ice-bath) under argon. After 5 minutes a solution of dichloromethyl methyl ether (17.08 g; 0.1485 mole) in 1,2-dichloroethane (135 ml) was added slowly over 30 minutes and the reaction mixture was stirred for a further 30 minutes in the ice-bath before being poured into ice water (500 ml). The mixture was shaken thoroughly and the organic layer was separated. The aqueous layer was extracted with 200 ml of 1,2-dichloroethane and the combined organic layers were washed with water (2×250 ml), dried (MgSO$_4$) and evaporated. The crude product 26.65 g (74.5%) consisted of a mixture of the two title compounds in the ratio of about 5:4 (by nmr).

The solid was suspended in hot ethyl acetate (135 ml) and the suspension was allowed to stand for several hours before collecting the solid. Recrystallization of this solid from acetonitrile gave pure 3-cyano-6-formyl-10,11-dihydrodibenzo[b,f]thiepin, m.p. 168°–9° C. crystallized in the form of pale yellow prisms, nmr (CDCl$_3$) 10.7 (s, CHO). Analysis for C$_{16}$H$_{11}$NOS Requires: C 72.43, H 4.18, N 5.28, S 12.08; Found: C 72.26, H 4.18, N 5.27, S 11.96.

Residue from the mother liquors were pooled and given a preliminary clean-up by chromatography on Merck silica gel using methylene chloride as solvent. The mixture of 6- and 8-formyl derivatives was separated by high pressure liquid chromatography on a Waters Prep Pak 500 instrument using methylene chloride. The 8-formyl derivative was the faster moving compound and complete separation was obtained with two recycles.

3-Cyano-8-formyl-10,11-dihydrodibenzo[b,f]thiepin crystallized from acetonitrile in colorless needles, m.p. 133°–134° C., nmr (CDCl$_3$) 9.90 (s, CHO).

Analysis for C$_{16}$H$_{11}$NOS Requires: C 72.43, H 4.18, N 5.28, S 12.08; Found: C 72.59, H 4.24, N 5.31, S 11.86.

EXAMPLE 14

Ethyl
3-(7-cyano-10,11-dihydrodibenzo[b,f]thiepin-4-yl)-2-ethoxycarbonyl propenoate A mixture of 3-cyano-6-formyl-10,11-dihydrodibenzo[b,f]thiepin (3.71 g, 14 mmole), diethyl malonate (2.285 g; 14.3 mmole), acetic acid (84 mg; 1.4 mmole), piperidine (119 mg; 1.4 mmole) and benzene (140 ml) was heated under reflux under a Dean Starck Trap for 24 hours. A further 64 mg of diethyl malonate was added and reflux was continued for 10 hours. Tne benzene was evaporated off under vacuum and the residue was dissolved in methylene chloride (75 ml). The solution was washed with water, dried (MgSO$_4$) and evaporated to a gum which soon crystallized. 6.521 g (theory 5.7 g).

Purification of a sample of the crude product by preparative thin layer chromatography (Whatman silica gel/methylene chloride) gave a recovery equivalent to a 96% yield, m.p. 96°–98° C.

Analysis for C$_{23}$H$_{21}$NO$_4$S Requires: C 67.79, H 5.19, N 3.44, S 7.87; Found: C 67.69, H 5.39, N 3.42, S 8.08.

EXAMPLE 15

Ethyl
3-(7-cyano-10,11-dihydrodibenzo[b,f]thiepin-2-yl)-2-ethoxycarbonyl propenoate Substituting 3-cyano-6-formyl-10,11-dihydrodibenzo[b,f]thiepin in the foregoing example with 3-cyano-8-formyl-10,11-dihydro-dibenzo[b,f]thiepin provides the title compound in 77% yield after chromatography (Whatman silica gel/5% ethyl acetate in methylene chloride). The compound melted at 132°–133° after recrystallization from ethyl acetate/isopropyl ether.

Analysis for: C$_{23}$H$_{21}$NO$_4$S Requires: C 67.79, H 5.19, N 3.44, S 7.87; Found: C 67.84, H 5.35, N 3.39, S 7.65.

EXAMPLE 16

Ethyl
3-(7-cyano-10,11-dihydrodibenzo[b,f]thiepin-2-yl)-2-ethoxycarbonyl propanoate A suspension of ethyl 3-(7-cyano-10,11-dihydrodibenzo[b,f]thiepin-2-yl)-2-ethoxycarbonylpropenoate (4.249 g; 10.44 mmole) in ethanol (130 ml) was treated with sodium borohydride (397 mg; 10.44 mole). The reaction mixture was stirred at room temperature until reduction is complete (ca 2 hours) and then it was acidified carefully with acetic acid. The solvent was evaporated and the residue was partitioned between water and methylene chloride. After washing the organic extract with saturated sodium chloride solution, it was evaporated to obtain an oil (4.125 g; 96%). The pure title compound was obtained by short path distillation of the crude product (oven temperature 230° C./0.05 Torr).

Analysis for: C$_{23}$H$_{23}$NO$_4$S Requires: C 67.46, H 5.66, N 3.43, S 7.83; Found: C 67.75, H 5.90, N 3.46, S 7.67.

EXAMPLE 17

Ethyl
3-(7-cyano-10,11-dihydrodibenzo[b,f]thiepin-4-yl)-2-ethoxycarbonyl propanoate Substituting ethyl 3-(7-cyano-10,11-dihydrodibenzo[b,f]thiepin-2-yl)-2-ethoxy carbonyl propenoate in the foregoing example with crude ethyl 3-(7-cyano-10,11-dihydrodibenzo[b,f]thiepin-4-yl)-2- ethoxycarbonyl propenoate provides the title compound in 69% yield m.p. 81°–83° C. after chromatography on Merck silica gel (90 g) using 3% ethyl acetate in methylene chloride for elution.

Analysis for C$_{23}$H$_{23}$NO$_4$S Requires: C 67.46, H 5.66, N 3.43, S 7.83; Found: C 67.46, H 5.76, N 3.29, S 7.78.

EXAMPLE 18

3-Cyano-6-hydroxymethyl-10,11-dihydrodibenzo[b,f]-thiepin
and
3-cyano-8-hydroxymethyl-10,11-dihydrodibenzo[b,f]-thiepin Sodium borohydride (42 mg; 1.1 mmole) was added portionwise to a mixture of 3-cyano-6-formyl-10,11-dihydrodibenzo[b,f]thiepin and 3-cyano-8-formyl-10,11-dihydrodibenzo[b,f]thiepin (from Example 13) (5:4 ratio) (236 mg; 0.89 mmole) in methanol (2.5 ml) and dimethylformamide (2.5 ml) under nitrogen. The reaction mixture was stirred one hour at room temperature, then poured slowly into ice. The precipitate was filtered off and air-dried to afford quantitatively a mixture of the two title compounds which are separated by thin layer chromatography (toluene/ethyl acetate: 7/3). The less polar compound being the 3-cyano-6-hydroxymethyl-10,11-dihydrodibenzo[b,f]thiepin, m.p. 150° C. and the more polar was the 3-cyano-8-hydroxymethyl-10,11-dihydrodibenzo[b,f]thiepin, m.p. 122° C.

EXAMPLE 19

3-Cyano-8-bromomethyl-10,11-dihydrodibenzo[b,f]-thiepin

Phosphorous tribromide (0.2 ml) was added to a suspension of 3-cyano-8-hydroxymethyl-10,11-dihydrodibenzo[b,f]thiepin (500 mg; 1.87 mmole) in ether (7 ml). The reaction mixture was stirred at room temperature for one hour, then poured onto ice, extracted with ether (3×50 ml), dried over $Na_2SO_4$ and evaporated to afford 581 mg (95%) of 3-cyano-8-bromomethyl-10,11-dihydrodibenzo[b,f]thiepin as an oil.

EXAMPLE 20

3-Cyano-6-bromomethyl-10,11-dihydrodibenzo[b,f]-thiepin

As described previously for the 3-cyano-8-bromomethyl-10,11-dihydrodibenzo[b,f]thiepin, the title compound was prepared from 3-cyano-6-hydroxymethyl-10,11-dihydrodibenzo[b,f]thiepin in 95% yield.

EXAMPLE 21

Ethyl 3-(7-cyano-10,11-dihydrodibenzo[b,f]thiepin-2-yl)-2-ethoxy carbonyl propanoate Diethylmalonate (0.69 ml; 4.5 mmoles) was added to a suspension of sodium hydride 50% in oil (220 mg; 4.58 mmoles) in dry dimethylformamide (3 ml) under nitrogen. The reaction mixture was stirred at room temperature for 30 minutes and added dropwise to a solution of 3-cyano-6-bromomethyl-10,11-dihydrodibenzo[b,f]thiepin (0.377 g; 0.8 mmole) in dry dimethylformamide (3 ml). The reaction mixture was stirred overnight at room temperature then poured on ice and extracted with methylene chloride (3×50 ml). The organic layer was dried ($Na_2SO_4$) and evaporated to dryness. The crude product was purified by column chromatography (E. Merck silica gel eluting with methylene chloride) affording 12 mg (25%) of pure title compound.

EXAMPLE 22

Ethyl 3-(7-cyano-10,11-dihydrodibenzo[b,f]thiepin-4-yl)-2-ethoxy carbonyl propanoate The title compound was obtained in 25% yield by the same route as the ethyl 3-(7-cyano-10,11-dihydrodibenzo[b,f]thiepin-2-yl)-2-ethoxy carbonyl propanoate starting with 3-cyano-8-bromomethyl-10,11-dihydrodibenzo[b,f]thiepin.

EXAMPLE 23

Ethyl 3-(7-cyano-10,11-dihydrodibenzo[b,f]thiepin-2-yl)propanoate

A mixture of ethyl 3-(7-cyano-10,11-dihydrodibenzo[b,f]thiepin-2-yl)-2-ethoxycarbonylpropanoate (4.025 g; 4.84 mmole), water (354 mg; 19.7 mmole), sodium chloride (576 mg) and dimethylsulfoxide (100 ml) are heated together under argon in an oil bath at 200°–205° C. for 3 hours. The cool reaction mixture was diluted with methylene chloride and the solution was extracted with water (3×100 ml), then dried ($MgSO_4$) and evaporated to an oil (3.223 g; 97%). The pure title compound was obtained by short path distillation of the crude product (oven temperature 200° C./0.05 Torr).

Analysis for: $C_{20}H_{19}NO_2S$ Requires: C 71.19, H 5.68, N 4.15, S 9.50; Found: C 71.18, H 5.91, N 4.10, S 9.47.

EXAMPLE 24

Ethyl 3-(7-cyano-10,11-dihydrodibenzo[b,f]thiepin-4-yl)propanoate

Substituting ethyl 3-(7-cyano-10,11-dihydrodibenzo[b,f]thiepin-2-yl)-2-ethoxycarbonylpropanoate in the foregoing example with an equivalent amount of ethyl 3-(7-cyano-10,11-dihydrodibenzo[b,f]-thiepin-4-yl-2-ethoxycarbonylpropanoate provided the title compound in 97% yield. The compound was purified by short-path distillation at an oven temperature of 190°/0.05 Torr and then has m.p. 61°–62° C. Analysis for: $C_{20}H_{19}NO_2S$ Requires: C 71.19, H 5.68, N 4.15, S 9.50; Found C 71.13, H 5.80, N 4.09, S 9.42.

EXAMPLE 25

8-(2-Carboxyethyl)-10,11-dihydrodibenzo[b,f]thiepin-3-carboxylic acid

A mixture of ethyl 3-(7-cyano-10,11-dihydrodibenzo[b,f]thiepin-2-yl)-propanoate (1.50 g, 4.45 mmole), ethanol (15 ml) and 40% potassium hydroxide solution (15 ml) was stirred under reflux under argon for 24 hours. The reaction mixture was diluted with water, acidified with hydrochloric acid and extracted with ethyl acetate (50 ml+2×25 ml). The extract was washed with water, then with saturated sodium chloride solution, dried ($MgSO_4$) and evaporated. Recrystallization of the crude product from acetic acid provided the title compound, 1.27 g, (87%), m.p. 233°–235° C.

Analysis for: $C_{18}H_{16}O_4S$ Requires: C 65.84, H 4.91, S 9.76; Found: C 65.61, H 4.77, S 9.53.

EXAMPLE 26

6-(2-Carboxyethyl)-10,11-dihydrodibenzo[b,f]thiepin-3-carboxylic acid

Substituting ethyl 3-(7-cyano-10,11-dihydrodibenzo[b,f]thiepin-2-yl)-propanoate in the foregoing Example 25 with an equivalent amount of ethyl 3-(7-cyano-10,11-dihydrodibenzo[b,f]thiepin-4-yl)-propanoate provided the title compound in 88% yield m.p. 265°–270° C. dec after recrystallization from acetic acid. Analysis for: $C_{18}H_{16}O_4S$ Requires: C 65.84, H 4.71, S 9.76; Found: C 65.68, H 5.02, S 9.48.

EXAMPLE 27

Methyl 1-oxo-2,3,9,10-tetrahydro-1H-benz[b]indeno[5,4-f]thiepin-6-carboxylate 6-(2-Carboxyethyl)-10,11-dihydrodibenz-[b,f]thiepin-3-carboxylic acid (328 mg; 1 mmole) was treated with thionyl chloride (6 ml) and after heating the mixture under reflux for 2 hours excess thionyl chloride was removed under vacuum. The residue was dissolved in 1,2-dichloroethane and the solvent was evaporated off to remove the last traces of thionyl chloride. The crude acid chloride dissolved in 1,2-dichloroethane (5 ml) was treated at 0°–5° C. with anhydrous aluminum chloride (100 mg; 0.75 mmole) in 1,2-dichloroethane (2 ml). The mixture was stirred in the ice-bath for 2 hours and then it was treated with methanol (4 ml). The mixture was stirred in the ice-bath for 5 minutes, then at room temperature for 30 minutes and finally at 50° C. for 30 minutes. Ethyl acetate (20 ml) was added and the solution was washed in succession with 2N hydrochloric acid (2×6 ml), water (6 ml), N sodium (2×6 ml) and finally with water (6 ml). Evaporation of the dried (MgSO$_4$) ethyl acetate solution gives 291 mg of crude product which on purification by column chromatography (10 g Merck silica gel eluted with 3% ethyl acetate in methylene chloride) gave 228 mg (70%) of solid m.p. 156°–158° C.

The pure title compound crystallized from acetonitrile in prisms m.p. 160°–161° C.

EXAMPLE 28

Methyl 1-oxo-2,3,11,12-tetrahydro-1H-benz[b]indeno-[4,5-f]thiepin-8-carboxylate and methyl 3-oxo-2,3,10,11-tetrahydro-1H-benz[b]indeno[5,6-f]thiepin-7-carboxylate Repetition of the procedure of Example 27 using an equivalent amount of 8-(2-carboxyethyl)-10,11-dihydrodibenz[b,f]thiepin-3-carboxylic acid in place of 6-(2-carboxyethyl)-10,11-dihydrodibenz-[b,f]thiepin-3-carboxylic acid provides a mixture of the two title compounds which are separated by column chromatography (Merck silica gel eluted with 3% ethyl acetate in methylene chloride). The first keto ester to be eluted was methyl 1-oxo-2,3,11,12-tetrahydro1H-benz[b]indeno[4,5-f]thiepin-8-carboxylate m.p. 162° C. (33%) and the second was methyl 3-oxo-2,3,10,11-tetrahydro-1H-benz[b]indeno[5,6-f]thiepin-7-carboxylate m.p. 218°–220° C. (20%).

EXAMPLE 29

1-Oxo-2,3,9,10-tetrahydro-1H-benz[b]indeno[5,4-f]thiepin-6-carboxylic acid

A solution of 85% potassium hydroxide (6.59 g) in water (60 ml) was diluted with ethanol (325 ml) and dioxane (32.5 ml).

Methyl 1-oxo-2,3,9,10-tetrahydro-1H-benz[b]indeno[5,4-f]thiepin-6-carboxylate (160 mg, 0.5 mmole) was added to 4.1 ml of the potassium hydroxide solution described above and the mixture was stirred at room temperature under argon for 8 hours. Water (2 ml) was added and then 10% hydrochloric acid (0.3 ml) was added to precipitate the title compound 126 mg (81%), m.p. 298°–302° (dec.).

EXAMPLE 30

1-Oxo-2,3,11,12-tetrahydro-1H-benz[b]indeno[4,5-f]thiepin-8-carboxylic acid

Repeating the procedure of Example 29 but using an equivalent amount of methyl 1-oxo-2,3,11,12-tetrahydro-1H-benz[b]indeno[4,5-f]thiepin-8-carboxylate in place of methyl 1-oxo-2,3,9,10-tetrahydro-1H-benz[b]indeno[5,4-f]thiepin-6-carboxylate provided the title compound in 79% yield, m.p. 267°–270° (dec.).

EXAMPLE 31

3-Oxo-2,3,10,11-tetrahydro-1H-benz[b]indeno[5,6-f]thiepin-7-carboxylic acid.

Repeating the procedure of Example 29 but using an equivalent amount of methyl 3-oxo-2,3,10,11-tetrahydro-1H-benz[b]indeno[5,6-f]thiepin-7-carboxylate in place of methyl 1-oxo-2,3,9,10-tetrahydro-1H-benz[b]indeno[5,4-f]thiepin-6-carboxylate provided the title compound.

EXAMPLE 32

(±)-1-Hydroxy-2,3,9,10-tetrahydro-1H-benzo[b]indeno-[5,4-f]thiepin-6-carboxylic acid A suspension of 1-oxo-2,3,9,10-tetrahydro-1H-benzo[b]indeno[5,4-f]thiepin-6-carboxylic acid (3.10 g, 10 mmole) in water (60 ml) was stirred during the addition of 1N sodium hydroxide solution (10 ml). After stirring for 15 minutes the mixture was treated with sodium borohydride (0.95 g, 25 mmole) in portions and the reaction mixture was stirred at room temperature overnight. Careful acidification of the mixture with 10% hydrochloric acid precipitated the racemic title compound which was collected by filtration and washed well with water.

EXAMPLE 33

(±)-1-Hydroxy-2,3,11,12-tetrahydro-1H-benzo[b]indeno-[4,5-f]thiepin-8-carboxylic acid Substituting an equivalent amount of 1-oxo-2,3,11,12-tetrahydro-1H-benzo[b]indeno[4,5-f]-thiepin-8-carboxylic acid in Example 32 for 1-oxo-2,3,9,10-tetrahydro-1H-benzo[b]indeno[5,4-f]thiepin-6-carboxylic acid provided the title compound.

EXAMPLE 34

(±)-3-Hydroxy-2,3,10,11-tetrahydro-1H-benzo[b]indeno-[5,6-f]thiepin-7-carboxylic acid Substituting an equivalent amount of 3-oxo-2,3,10,11-tetrahydro-1H-benzo[b]indeno[5,6-f]thiepin-7-carboxylic acid in Example 32 for 1-oxo-2,3,9,10-tetrahydro-1H-benzo[b]indeno[5,4-f]thiepin-6-carboxylic acid provided the title compound.

EXAMPLE 35

(±)-1α-Hydroxy 4α-oxido-2,3,9,10-tetrahydro-1H-benzo-[b]indeno[5,4-f]thiepin-6-carboxylic acid and (±)-1β-hydroxy-4α-oxido-2,3,9,10-tetrahydro-1H-benzo[b]-indeno-[5,4-f]thiepin-6-carboxylic acid STEP A: Preparation of methyl 1-hydroxy-2,3,9,10-tetrahydro-1H-benzo[b]indeno[5,4-f]thiepin-6-carboxylate A suspension of (±)-1-hydroxy-2,3-9-10-tetrahydro-1H-benzo[b]indeno[5,4-f]thiepin-6-carboxylic acid (3.10 g; 10 mmole) in methanol (30 ml) at room temperature was treated with excess ethereal diazomethane solution in small portions with stirring. The completion of the reaction was indicated by the cessation of the evolution of nitrogen after adding more diazomethane and was confirmed by thin layer chromatography. Evaporation of the solvent provided the title compound. [Note: An alternative method of preparation was by reduction of methyl 1-oxo-2,3,9,10-tetrahydro-1H-benzo-[b]indeno[5,4-f]thiepin-6-carboxylate.]

STEP B: Preparation of methyl (±)-1α-hydroxy-4α-oxido-2,3,9,10-tetrahydro-1H-benzo[b]indeno-[5,4-f]thiepin-6-carboxylate and methyl (±)-1β-hydroxy-4α-oxido-2,3,9,10-tetrahydro-1H-benzo[b]indeno[5,4-f]thiepin-6-carboxylate A solution of methyl (±)-1-hydroxy-2,3,9,10-tetrahydro-1H-benzo[b]indeno[5,4-f]thiepin-6-carboxylate (1.40 g, 4 mmole) in methylene chloride (70 ml) was treated at 0°–5° C. with 85% m-chloroperbenzoic acid (2.13 g, 4.2 mmole) in small portions. After stirring the mixture for 2 hours calcium hydroxide (4.25 g) was added and after another 20 mins. the solution was filtered. Evaporation of the solvent afforded a mixture of the diastereoisomeric methyl esters which are separated by column chromatography to provide the individual title compounds.

STEP Ci: Preparation of (±)-1α-hydroxy-4α-oxido-2,3,9,10-tetrahydro-1H-benzo[b]indeno-[5,6-f]-thiepin-6-carboxylic acid Substituting an equivalent amount of methyl (±)-1α-hydroxy-4α-oxido-2,3,9,10-tetrahydro-1H-benzo-[b]indeno[5,4-f]thiepin-6-carboxylate in Example 29 for methyl 1-oxo-2,3,9,10-tetrahydro-1H-benzo[b]indeno[5,4-f]thiepin-6-carboxylate provided the title compound.

STEP Cii: Preparation of (±)-1β-hydroxy-4α-oxido-2,3,9,10-tetrahydro-1H-benzo[b]indeno-[5,4-f]thiepin-6-carboxylic acid Substituting an equivalent amount of methyl(±)-1β-hydroxy-4α-oxido-2,3,9,10-tetrahydro-1H-benzo[b]indeno[5,4-f]thiepin-6-carboxylate in Example 29 for methyl 1-oxo-2,3,9,10-tetrahydro-1H-benzo-[b]indeno[5,4-f]thiepin-6-carboxylate provided the diastereoisomer of the product from Step Ci.

EXAMPLE 36

(±)-1α-Hydroxy-6α-oxido-2,3,11,12-tetrahydro-1H-benzo[b]indeno[4,5-f]thiepin-8-carboxylic acid and (±)-1β]Hydroxy-6α-oxido-2,3,11,12-tetrahydro-1H-benzo[b]-indeno[4,5-f]thiepin-8-carboxylic acid Substituting an equivalent amount of (±)-1-hydroxy-2,3,11,12-tetrahydro-1H-benzo[b]indeno[4,5-f]-thiepin-8-carboxylic acid in Example 35, Step A, in place of (±)-1-hydroxy-2,3,9,10-tetrahydro-1H-benzo[b]indeno[5,4-f]thiepin-6-carboxylic acid and then proceeding through Steps B, Ci and Cii provided the diastereoisomeric title compounds.

EXAMPLE 37

(±)-3α-Hydroxy-5α-oxido-2,3,10,11-tetrahydro-1H-benzo[b]indeno[5,6-f]thiepin-7-carboxylic acid and (±)-3β-Hydroxy-5α-oxido-2,3,10,11-tetrahydro-1H-benzo[b]indeno[5,6-f]thiepin-7-carboxylic acid Substituting an equivalent amount of (±)-3-hydroxy-2,3,10,11-tetrahydro-1H-benzo[b]indeno[5,6-f]thiepin-7-carboxylic acid in Example 35, Step A, in place of 1-hydroxy-2,3,9,10-tetrahydro-1H-benzo [b]indeno[5,4-f]thiepin-6-carboxylic acid and then proceeding through Steps B, Ci and Cii provided the title compounds.

EXAMPLE 38

4-Oxido-1-oxo-2,3,9,10-tetrahydro-1H-benzo[b]indeno-[5,4-f]thiepin-6-carboxylic acid STEP A: Preparation of methyl 4-oxido-1-oxo-2,3,9,10-tetrahydro-1H-benzo[b]indeno[5,4-f]thiepin-6-carboxylate m-Chloroperbenzoic acid (85%) (10 mg; 0.05 mmole) was added to a solution of methyl 1-oxo-2,3,9,10-tetrahydro-1H-benzo[b]indeno[5,4-f]thiepin-6-carboxylate (16 mg; 0.05 mmole) in methylene chloride (5 ml) stirred in an ice-bath. The reaction mixture was allowed to warm to 10° C. and monitored by thin layer chromatography. A very small additional quantity of peracid was added to complete the oxidation. Calcium hydroxide (25 mg) was added and after stirring the mixture for 15 mins. it was filtered and evaporated to afford the title compound as a solid, m.p. 227°–229° C. dec.

STEP B: Preparation of 4-oxido-1-oxo-2,3,9,10-tetrahydro-1H-benzo[b]indeno[5,4-f]thiepin-5-carboxylic acid Substituting an equivalent amount of methyl 4-oxido-1-oxo-2,3,9,10-tetrahydro-1H-benzo[b]indeno[5,4-f]thiepin-6-carboxylate in Example 29 in place of methyl 1-oxo-2,3,9,10-tetrahydro-1H-benzo[b]-indeno[5,4-f]thiepin-6-carboxylate provided the title compound.

EXAMPLE 39

6-Oxido-1-oxo-2,3,11,12-tetrahydro-1H-benzo[b]indeno[4,5-f]thiepin-8-carboxylic acid Substituting an equivalent amount of methyl 1-oxo-2,3,11,12-tetrahydro-1H-benzo[b]indeno[4,5-f]-thiepin-8-carboxylate in Example 38, Step A, in place of methyl 1-oxo-2,3,9,10-tetrahydro-1H-benzo[b]-indeno[5,4-f]thiepin-6-carboxylate and taking the product through Step B of this example provided the title compound.

EXAMPLE 40

5-Oxido-3-oxo-2,3,10,11-tetrahydro-1H-benzo[b]indeno[5,6-f]thiepin-7-carboxylic acid Substituting an equivalent amount of methyl 3-oxo-2,3,9,10-tetrahydro-1H-benzo[b]indeno[5,4-f]thiepin-6-carboxylate in Example 38, Step A, in place of methyl 1-oxo-2,3,9,10-tetrahydro-1H-benzo[b]-indeno[5,4-f]thiepin-6-carboxylate and then taking the product through Step B of this example provided the title compound.

EXAMPLE 41

2,3,11,12-Tetrahydro-1H-benzo[b]indeno[4,5-f]thiepin-8-carboxylic acid

1-Oxo-2,3,11,12-tetrahydro-1H-benzo[b]indeno[4,5-f]thiepin-8-carboxylic acid (50 mg; 0.16 mmole) was added in portions over a ¾ hour period to a refluxing mixture of acetic acid (4 ml), concentrated hydrochloric acid (0.3 ml) and amalgamated "mossy" zinc (220 mg) under argon. After a further 3 hours under reflux no oxo-acid remained. The reaction mixture was filtered, evaporated to a small volume and diluted with a little water to afford 43 mg of the title compound.

On esterification with diazomethane this acid gave a methyl ester of m.p. 88° C.

EXAMPLE 42

2,3,9,10-Tetrahydro-1H-benzo[b]indeno[5,4-f]thiepin-6-carboxylic acid

Substituting an equivalent amount of 1-oxo2,3,9,10-tetrahydro-1H-benzo[b]indeno[5,4-f]thiepin-6-carboxylic acid in Example 41 in place of 1-oxo2,3,11,12-tetrahydro-1H-benzo[b]indeno[4,5-f]thiepin-8-carboxylic acid and heating under reflux for 9 hours instead of 3 hours yielded the title compound.

The methyl ester of this product had a m.p. of 77° C.

Although the instant invention has been described in the foregoing specification in terms of the use of the novel oxathiepins disclosed herein in the treatment and control of human and warm-blooded animal disease conditions characterized by excessive undesirable contractile activity of prostaglandins and prostaglandin biosynthetic intermediates, and particularly of asthma, it will be recognized by those skilled in the art that, in addition to the involvement of contractile prostaglandins in chronic obstructive lung disease (e.g. asthma), prostaglandins play a role in other allergic conditions as well as in inflammation, diarrhea, hypertension, angina, platelet aggregation, cerebral spasm, premature abortion and dismenorrhea. Also the oxathiepins of this invention are potent $TXA_2$ biosynthesis inhibitors, inhibiting platelet aggregation, and can be useful in diseases such as atherosclerosis, and myocardial infarction. Applicants consider application of the oxathiepins disclosed and claimed herein to the treatment and control of such disease conditions to be obvious equivalents to the invention as disclosed by applicants and to fall within the scope of the instant invention.

For those compounds in which asymmetry is present, the present invention includes both the racemic forms and the separate optically active isomers thereof.

The subject matter which applicants regard as their invention, and which is sought to be patented herein, is particularly pointed out and distinctly claimed as follows.

What is claimed is:

1. A compound selected from the group consisting of dibenz thiepins having the structural formulae:

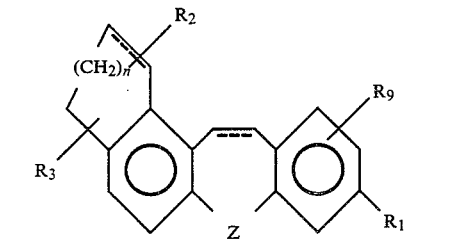

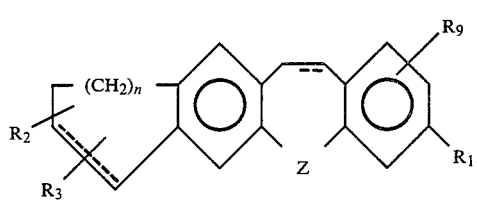

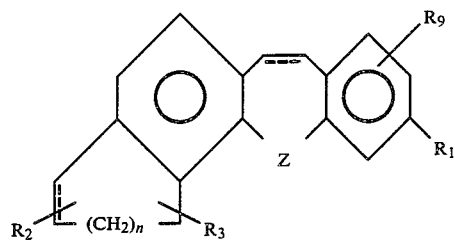

wherein
n is 1 of 2; the broken lines represent optional double bonds;

Z is a member selected from the group consisting of thio, sulfinyl, and sulfonyl;

$R_2$, $R_3$ and $R_9$ are the same or different and are members selected from the group consisting of hydrogen, halogen loweralkyl, loweralkanoyl, hydroxy, loweralkoxy, loweralkylthio, trifluoromethylthio, loweralkylsulfinyl, loweralkylsulfonyl, trifluoromethyl or $R^2$ and $R^3$ may together represent a double bonded oxygen;

$R_1$ is a member selected from the groups consisting of
(a) 5-tetrazolyl, and $$-(CH_2)_m-\overset{O}{\underset{\|}{C}}-R_4$$

wherein m is an integer of from 0 to 4 and $R_4$ is a member selected from the group consisting of hydroxy, loweralkoxy or amino
(b) —CHO
(c) —$(CH_2)_m$—$OR_8$ wherein m is 0–4 and $R_8$ is hydrogen and the pharmaceutically acceptable salts thereof.

2. The compounds of claim 1:
Ethyl 2,3-Dihydro-1H-benzo[b]indeno[5,6-f]thiepin-7-carboxylate;
2,3-Dihydro-1H-benzo[b]indeno[5,6-f]thiepin-7-carboxylic acid;
2,3-Dihydro-1H-benzo[b]indeno[5,6-f]thiepin-7-carboxylic acid 5-oxide;
5-(2,3-Dihydro-1H-benzo[b]indeno[5,6-f]thiepin-7-yl) tetrazole;
2,3-Dihydro-1H-benzo[b]indeno[5,6-f]thiepin-7-carboxamide;
5-(2,3-Dihydro-1H-benzo[b]indeno[5,6-f]thiepin-7-yl)-tetrazole;
5-(2,3-Dihydro-5-oxido-1H-benzo[b]indeno[5,6-f]thiepin-7-yl)-tetrazole;
5-(2,3-Dihydro-5,5-dioxido-1H-benzo[b,f]thiepin-7-yl)-tetrazole;
2,3,10,11-Tetrahydro-1H-benzo[b]indeno[5,6-f]thiepin-7-carboxylic acid;
2,3,10,11-Tetrahydro-1H-benzo[b]indeno[5,6-f]-thiepin-7-carboxylic acid 5-oxide;
Methyl 2,3,10,11-tetrahydro-1H-benzo[b]-indeno[5,6-f]-thiepin-7-carboxylate;
Methyl 2,3,10,11-tetrahydro-1H-benzo[b]indeno[5,6-f]-thiepin-7-carboxylate-5-oxide;
2,3,10,11-Tetrahydro-1H-benzo[b]indeno[5,6-f]thiepin-7-carboxylic acid 5,5-dioxide;
Methyl 2,3,10,11-tetrahydro-1H-benzo[b]indeno-[5,6-f]thiepin-7-carboxylate 5,5-dioxide;

Methyl 1-oxo-2,3,9,10-tetrahydro-1H-benz[b]-indeno[5,4-f]thiepin-6-carboxylate;
Methyl 1-oxo-2,3,11,12-tetrahydro-1H-benz[b]indeno-[4,5-f]thiepin-8-carboxylate;
Methyl 3-oxo-2,3,10,11-tetrahydro-1H-benz[b]indeno [5,6-f]thiepin-7-carboxylate;
1-Oxo-2,3,9,10-tetrahydro-1H-benz[b]indeno[5,4-f]thiepin-6-carboxylic acid;
1-Oxo-2,3,11,12-tetrahydro-1H-benz[b]indeno[4,5-f]thiepin-8-carboxylic acid;
3-Oxo-2,3,10,11-tetrahydro-1H-benz[b]indeno[5,6-f]thiepin-7-carboxylic acid;
(±)-1-Hydroxy-2,3,9,10-tetrahydro-1H-benzo[b]indeno[5.4-f,]thiepin-6-carboxylic acid;
(±)-1-Hydroxy-2,3,11,12-tetrahydro-1H-benzo[b]indeno-[4,5-f]thiepin-8-carboxylic acid;
(±)-3-Hydroxy-2,3,10,11-tetrahydro-1H-benzo[b]indeno-[5,6-f]thiepin-7-carboxylic acid;
(±)-1α-Hydroxy 4α-oxido-2,3,9,10-tetrahydro-1H-benzo-[b]indeno[5,4-f]thiepin-6-carboxylic acid;
(±)-1β-Hydroxy-4α-oxido-2,3,9,10-tetrahydro-1H-benzo-[b]indeno-[5,4-f]thiepin-6-carboxylic acid;
Methyl 1-hydroxy-2,3,9,10-tetrahydro-1H-benzo[b]-indeno[5,4-f]thiepin-6-carboxylate;
Methyl (±)-1α-hydroxy-4α-oxido-2,3,9,10-tetrahydro-1H-benzo[b]indeno[5,4-f]thiepin-6-carboxylate; Methyl
(±)-1β-Hydroxy-4α-oxido-2,3,9,10-tetrahydro-1H-benzo-[b]indeno[5,4-f]thiepin-6-carboxylate;
(±)-1α-Hydroxy-4α-oxido-2,3,9,10-tetrahydro-1H-benzo-[b]indeno[5,6-f]-thiepin-6-carboxylic acid;
(±)-1β-hydroxy-4α-oxido-2,3,9,10-tetrahydro-1H-benzo-[b]indeno[5,4-f]thiepin-6-carboxylic acid;
(±)-1α-Hydroxy-6α-oxido-2,3,11,12-tetrahydro-1H-benzo[b]indeno[4,5-f]thiepin-8-carboxylic acid;
(±)-1β-Hydroxy-6α-oxido-2,3,11,12-tetrahydro-1H-benzo[b]-indeno[4,5-f]thiepin-8-carboxylic acid;
(±)-3α-Hydroxy-5α-oxido-2,3,10,11-tetrahydro-1H-benzo[b]indeno[5,6-f]thiepin-7-carboxylic acid;
(±)-3β-Hydroxy-5α-oxido-2,3,10,11-tetrahydro-1H-benzo[b]indeno[5,6-f]thiepin-7-carboxylic acid;
4-Oxido-1-oxo-2,3,9,10-tetrahydro-1H-benzo[b]indeno-[5,4-f]thiepin-6-carboxylic acid;
Methyl 4-oxido-1-oxo-2,3,9,10-tetrahydro-1H-benzo[b]indeno[5,4-f]thiepin-6-carboxylate;
6-Oxido-1-oxo-2,3,11,12-tetrahydro-1H-benzo[b]indeno[4,5-f]thiepin-8-carboxylic acid;
5-Oxido-3-oxo-2,3,10,11-tetrahydro-1H-benzo[b]indeno[5,6-f]thiepin-7-carboxylic acid;
Methyl 2,3,11,12-tetrahydro-1H-benzo[b]indeno[4,5-f]thiepin-8-carboxylate;
2,3,11,12-Tetrahydro-1H-benzo[b]indeno[4,5-f]thiepin-8-carboxylic acid;
Methyl 2,3,9,10-tetrahydro-1H-benzo[b]indeno[5,4-f]thiepin-6-carboxylate;
2,3,9,10-Tetrahydro-1H-benzo[b]indeno[5,4-f]thiepin-6-carboxylic acid.

3. A compound of claim 1 wherein Z is sulfonyl, $R_2$ and $R_3$ are hydrogen and $R_1$ is a member selected from the group consisting of 5-tetrazolyl and

4. A compound of claim 1 wherein Z is thio, $R_2$ and $R_3$ are hydrogen and $R_1$ is a member selected from the group consisting of 5-tetrazolyl and

5. A compound of claim 4 wherein $R_1$ is 5-tetrazolyl.
6. The compound of claim 5 which is 5-(2,3-dihydro-1H-benzo[b]indeno[5,6-f]thiepin-7-yl)-tetrazole.
7. A compound of claim 4 wherein $R_1$ is

8. The compound of claim 7 which is methyl 1-oxo-2,3,9,10-tetrahydro-1H-benz[b]indeno [5,4-f]thiepin-6-carboxylate.
9. The compound of claim 7 which is 2,3,10,11-tetrahydro-1H-benzo[b]indeno[5,6-f]thiepin-7-carboxylic acid.
10. The compound of claim 7 which is methyl 1-oxo-2,3,11,12-tetrahydro-1H-benz[b]indeno-[4,5-f]thiepin-8-carboxylate.
11. The compound of claim 7 which is methyl 3-oxo-2,3,10,11-tetrahydro-1H-benz[b]indeno[5,6-f]-thiepin-7-carboxylate.
12. A compound of claim 7 wherein $R_4$ is hydroxy.
13. The compound of claim 12 which is 1-oxo-2,3,9,10-tetrahydro-1H-benz[b]indeno[5,4-f]-thiepin-6-carboxylic acid.
14. A compound of claim 12 which is 1-oxo-2,3,11,12-tetrahydro-1H-benz[b]indeno[4,5-f]thiepin-8-carboxylic acid.
15. The compound of claim 12 which is 3-oxo-2,3,10,11-tetrahydro-1H-benz[b]indeno[5,6-f]-thiepin-7-carboxylic acid.
16. The compound of claim 12 which is 2,3-dihydro-1H-benzo[b]indeno[5,6-f]thiepin-7-carboxylic acid.
17. A compound of claim 1 wherein Z is sulfinyl, $R_2$ and $R_3$ are hydrogen and $R_1$ is a member selected from the group consisting of 5-tetrazolyl and:

18. A compound of claim 17 wherein $R_1$ is 5-tetrazolyl.
19. The compound of claim 18 which is 5-(2,3-dihydro-5-oxido-1H-benzo[b]indeno[5,6-f]thiepin-7-yl)tetrazole.
20. A compound of claim 17 wherein $R_1$ is

21. A compound of claim 20 wherein $R_4$ is hydroxy.
22. The compound of claim 21 which is 2,3-dihydro-1H-benzo[b]indeno[5,6-f]thiepin-7-carboxylic acid 5-oxide.
23. The compound of claim 21 which is 2,3,10,11-tetrahydro-1H-benzo[b]indeno[5,6-f]thiepin-7-carboxylic acid 5-oxide.
24. A compound of claim 3 wherein $R_1$ is 5-tetrazolyl.
25. The compound of claim 24 which is 5-(2,3-dihydro-5,5-dioxido-1H-benzo[b,f]thiepin-7-yl)-tetrazole.
26. A compound of claim 3 wherein $R_1$ is

27. A compound of claim 26 wherein $R_4$ is hydroxy.
28. The compound of claim 26 which is 2,3-dihydro-1H-benzo[b]indeno[5,6-f]thiepin-7-carboxylic acid 5,5-dioxide
29. The compound of claim 26 which is 2,3,10,11-tetrahydro-1H-benzo[b]indeno[5,6-f]thiepin-7-carboxylic acid 5,5-dioxide.
* * * * *

UNITED STATES PATENT AND TRADEMARK OFFICE
CERTIFICATE OF CORRECTION

PATENT NO. : 4,622,403
DATED : November 11, 1986
INVENTOR(S) : HAYDN WILLIAMS and JOSHUA ROKACH It is certified that error appears in the above—identified patent and that said Letters Patent is hereby corrected as shown below:

In Column 24, line 14; (Claim 1): -

1 of 2 should read -- 1 or 2

Signed and Sealed this

Twenty-fourth Day of March, 1987

Attest:

DONALD J. QUIGG

Attesting Officer

Commissioner of Patents and Trademarks